United States Patent [19]

Hageman et al.

[11] Patent Number: 4,548,638

[45] Date of Patent: Oct. 22, 1985

[54] HERBICIDAL SULFONYLUREAS

[75] Inventors: Larry H. Hageman, Claymont; Gerald A. Roy, Jr., Wilmington, both of Del.

[73] Assignee: E. I. Du Pont de Nemours and Company, Wilmington, Del.

[21] Appl. No.: 525,506

[22] Filed: Aug. 22, 1983

[51] Int. Cl.⁴ .................... C07D 251/52; A01N 43/70
[52] U.S. Cl. .................................. 71/93; 544/208
[58] Field of Search .......................... 544/208; 71/93

[56] References Cited

U.S. PATENT DOCUMENTS

| 4,127,405 | 11/1978 | Levitt | 71/93 |
| 4,310,346 | 1/1982 | Levitt et al. | 71/92 |
| 4,383,113 | 5/1983 | Levitt | 544/211 |
| 4,417,917 | 11/1983 | Levitt et al. | 544/211 |
| 4,435,205 | 3/1984 | Reap | 544/212 |

FOREIGN PATENT DOCUMENTS

| 0044212 | 7/1981 | European Pat. Off. | 239/42 |
| 827439 | 10/1982 | South Africa . | |

Primary Examiner—John M. Ford

[57] ABSTRACT

Designated sulfonylureas which contain amino-substituted heterocyclic rings provide unexpected selectivity for rape.

16 Claims, No Drawings

HERBICIDAL SULFONYLUREAS

BACKGROUND OF THE INVENTION

This invention relates to certain sulfonylureas having amino-substituted heterocyclic rings which show selectivity for rape.

In U.S. Pat. No. 4,127,405, compounds are disclosed of the general formula:

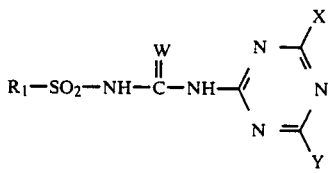

wherein $R_1$ is

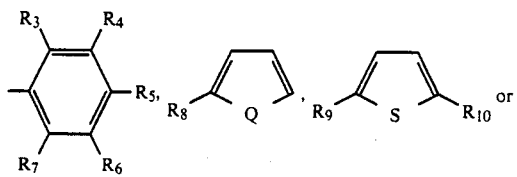

$R_3$ and $R_6$ are independently hydrogen, fluorine, chlorine, bromine, iodine, akyl of 1–4 carbon atoms, alkoxy of 1–4 carbon atoms, nitro, trifluoromethyl, cyano, $CH_3S(O)_n$— or $CH_3CH_2S(O)_n$—;

$R_4$ is hydrogen, fluorine, chlorine, bromine or methyl;

$R_5$ is hydrogen, fluorine, chlorine, bromine, methyl or methoxy;

$R_7$ is hydrogen, fluorine, chlorine, bromine, alkyl of 1–2 carbon atoms or akoxy of 1–2 carbon atom;

$R_8$ is hydrogen, methyl, chlorine or bromine;

$R_9$ and $R_{10}$ are independently hydrogen, methyl, chlorine or bromine;

W and Q are independently oxygen or sulfur;

n is 0, 1 or 2;

X is hydrogen, chlorine, bromine, methyl, ethyl, alkoxy of 1–3 carbon atoms, trifluoromethyl, $CH_3S$— or $CH_3OCH_2$—; and Y is methyl or methoxy; or their agriculturally suitable salts; provided that:

(a) when $R_5$ is other than hydrogen, at least one of $R_3$, $R_4$, $R_6$ and $R_7$ is other than hydrogen and at least two of $R_3$, $R_4$, $R_6$ and $R_7$ must be hydrogen;

(b) when $R_5$ is hydrogen and all of $R_3$, $R_4$, $R_6$ and $R_7$ are other than hydrogen, then all of $R_3$, $R_4$, $R_6$ and $R_7$ must be either chlorine or methyl; and (c) when $R_3$ and $R_7$ are both hydrogen, at least one of $R_4$, $R_5$ or $R_6$ must be hydrogen.

In particular, the patent discloses orthosubstituted compounds wherein the substitution is $C_1$–$C_4$ alkyl.

In U.S. Pat. No. 4,383,113, compounds are disclosed of the general formula:

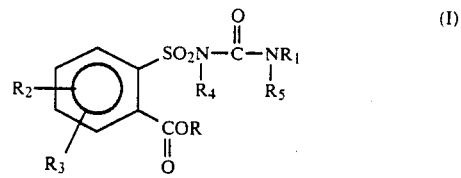

wherein

R may be $C_1$-$C_{12}$ alkyl, $C_3$-$C_{10}$ alkenyl or $C_2$-$C_6$ alkyl substituted with halogen;

$R_2$ and $R_3$ may be hydrogen, as may $R_4$ and $R_5$;

$R_1$ may be

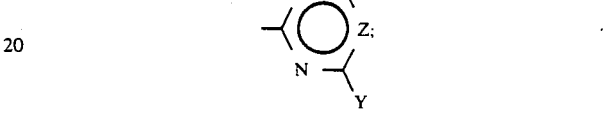

$R_2$ is H, Cl, Br, F, $C_1$-$C_3$ alkyl, —$NO_2$, —$SO_2CH_3$, —$OCH_3$, —$SCH_3$, —$CF_3$, —$N(CH_3)_2$, —$NH_2$ or —CN;

$R_3$ is H, Cl, Br, F or —$CH_3$;

$R_4$ is H or —$CH_3$;

$R_5$ is H, —$CH_3$ or —$OCH_3$;

Z is N;

X is H, Cl, —$CH_3$, —$OCH_3$, —$OCH_2CH_3$ or —$OCH_2CH_2OCH_3$;

Y may be H; Cl; $C_1$-$C_4$ alkyl; $C_1$-$C_4$ alkyl substituted with —$OCH_3$, —$OC_2H_5$, —CN, —$CO_2CH_3$, —$CO_2C_2H_5$, or 1 to 3 atoms of F, Cl, Br; or $NR_{16}R_{17}$ where $R_{16}$ is H or $CH_3$ and $R_{17}$ may be H, $OCH_3$ or $C_1$-$C_6$ alkyl.

U.S. Pat. No. 4,310,346, teaches herbicidal triazine sulfonylureas containing ortho-sulfamoyl groups.

EPO Publication No. 44,212 (published Jan. 20, 1982) teaches herbicidal triazine sulfonylureas containing ortho-sulfonate groups.

None of the above disclosures teaches compounds which are selective for rape.

Rape, also known as canola, is an annual broadleaf crop grown for its oil and use as a seed meal. Rape is a member of the genus Brassica and commonly includes *Brassica napus* (rape or oilseed rape) and *Brassica campestris* (fodder rape or turnip rape). Rape oil is used in a wide range of food products including ice cream, lard, margarine and chocolate. The extracted rape seed meal is used as a livestock feed.

The genus Brassica also includes other important crop plants such as broccoli, cauliflower, Brussel sprouts and cabbage.

With the current population explosion and concomitant world food shortage, improvements in efficiency of producing a crop such as rape is extremely important. Prevention or minimization of the loss of a portion of such a valuable crop by killing, or inhibiting the growth of undesired vegetation is one way of improving the crop yields.

SUMMARY OF THE INVENTION

According to this invention, it has unexpectedly been found that a small number of sulfonylurea compounds possess selective rape herbicidal activity.

This invention pertains to sulfonylurea herbicides of Formula I, agriculturally suitable compositions containing them and their method of use as selective pre-emergence or post-emergence herbicides for the control of weeds often found in conjunction with rape, without damaging the desired crop, rape.

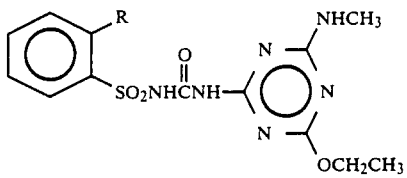

wherein
R is $CO_2CH_3$, $CO_2CH_2CH_3$, $CO_2CH_2CH_2CH_3$, $CO_2CH_2CH=CH_2$, $CO_2CH(CH_3)_2$, $CO_2CH_2CH_2Cl$, $SO_2N(CH_3)_2$ or $OSO_2CH_3$.

Preferred for reasons of their higher herbicidal activity with concurrent safety to rape and/or more favorable ease of synthesis are:

(1) Compounds of Formula I where R is $CO_2CH_3$, $CO_2CH_2CH_3$, $CO_2CH_2CH_2CH_3$, $CO_2CH_2CH=CH_2$, $CO_2CH(CH_3)_2$, $CO_3CH_2CH_2Cl$ or $OSO_2CH_3$.

(2) Compounds of Preferred 1 where R is $CO_2CH_3$, $CO_2CH_2CH_3$ or $OSO_2CH_3$.

Specifically preferred for reasons of their highest herbicidal activity and/or most favorable ease of synthesis are:

2-[[(4-ethoxy-6-methylamino-1,3,5-triazin-2-yl)aminocarbonyl]aminosulfonyl]benzoic acid, methyl ester, m.p. 204°–206° C.;

2-[[(4-ethoxy-6-methylamino-1,3,5-triazin-2-yl)aminocarbonyl]aminosulfonyl]benzoic acid, ethyl ester, m.p. 212°–215° C.; and N-[(4-ethoxy-6-methylamino-1,3,5-triazin-2-yl)aminocarbonyl]-2-methylsulfonyloxybenzenesulfonamide, m.p. 178°–180° C.

DETAILED DESCRIPTION OF THE DISCLOSURE

Synthesis

The compounds of Formula I which are, unexpectedly, selective pre-emergent or post-emergent herbicides for weed control in rape are prepared, as shown in Equation 1, by the reaction of an appropriately substituted sulfonyl isocyanate of Formula II with 4-ethoxy-6-methylamino-1,3,5-triazin-2-amine (Formula III), by methods described in U.S. Pat. No. 4,383,113.

Equation 1

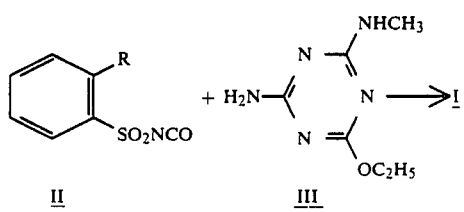

The sulfonyl isocyanates of Formula II are known in the art. They are prepared by methods described in U.S. Pat. No. 4,238,621, U.S. Pat. No. 4,310,346 and European Patent Application No. 44,212.

The aminotriazine of Formula III is known in the art, see *J. Amer. Chem. Soc.*, 71, 3248 (1949).

The following example further teaches the preparation of compounds of Formula I.

The reaction takes place at a temperature of 5° to 100° C., preferably 20° to 50° C., over a period of 0.5 to 48 hours, preferably 1 to 24.

In the following example, all temperatures are in °C. unless otherwise specified.

EXAMPLE 1

Methyl 2-[[(4-ethoxy-6-methylamino-1,3,5-triazin-2-yl)aminocarbonyl]aminosulfonyl]benzoate To a suspension of 0.8 g of 4-ethoxy-6-methylamino-1,3,5-triazin-2-amine in 25 ml of methylene chloride was added 1.14 g of 2-(methoxycarbonyl)benzenesulfonyl isocyanate. Dissolution of the suspension occurred, followed by precipitation of a solid. After 1 hour at ambient temperature, the solid was collected and dried giving 0.9 g of the title compound, m.p. 204°–206° C.

IR (nujol mull) C=O (1700 and 1730 cm$^{-1}$).

The other selective herbicides of Formula I of this invention are listed in Table I.

Using the procedure of Example 1, one skilled in the art can produce the compounds of Table I.

TABLE I

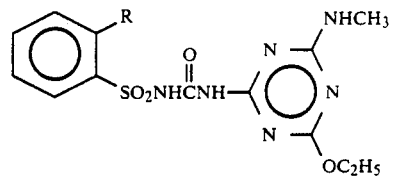

| R | m.p. (°C.) |
|---|---|
| $CO_2C_2H_5$ | 212–215° |
| $CO_2CH_2CH_2CH_3$ | 185–187° |
| $CO_2CH_2CH=CH_2$ | 177–180° |
| $CO_2CH(CH_3)_2$ | 160–163° |
| $CO_2CH_2CH_2Cl$ | 166–169° |
| $SO_2N(CH_3)_2$ | 169–171° |
| $OSO_2CH_3$ | 177–180° |

Formulations

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid inert diluent(s). More specifically, they will contain these ingredients in the following approximate proportions:

TABLE II

| Active Ingredient | Weight Percent* | | |
|---|---|---|---|
| | | Diluent(s) | Surfactant(s) |
| Wettable Powders | 20–90 | 0–74 | 1–10 |
| Oil Suspensions, Emulsions, Solutions, | 3–50 | 40–95 | 0–15 |

TABLE II-continued

|  | Active Ingredient | Weight Percent* Diluent(s) | Surfactant(s) |
|---|---|---|---|
| (including Emulsifiable Concentrates) |  |  |  |
| Aqueous Suspension | 10–50 | 40–84 | 1–20 |
| Dusts | 1–25 | 70–99 | 0–5 |
| Granules and Pellets | 0.1–95 | 5–99.9 | 0–15 |
| High Strength Compositions | 90–99 | 0–10 | 0–2 |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", *Chemical Engineering*, Dec. 4, 1967, pp. 147ff. and "Perry's Chemical Engineer's Handbook", 5th Ed., McGraw-Hill, New York, 1973, pp. 8-57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138–140, 162–164, 166, 167 and 169–182;

H. Gysin and E. Knusli, U.S. Pat. No. 2,891,855, June 23, 1959, Col. 3, line 66 through Col. 5, line 17 and Examples 1–4;

G. C. Klingman, "Weed Control as a Science", John Wiley and Sons, Inc., New York, 1961, pp. 81–96; and J. D. Fryer and S. A. Evans, "Weed Control Handbook", 5th Ed., Blackwell Scientific Publications, Oxford, 1968, pp. 101–103.

In the following examples, all parts are by weight unless otherwise indicated.

EXAMPLE 2

Wettable Powder

2-[[(4-ethoxy-6-methylamino-1,3,5-triazin-2-yl)-aminocarbonyl]aminosulfonyl]benzoic acid, methyl ester: 80%
sodium alkylnaphthalenesulfonate: 2%
sodium ligninsulfonate: 2%
synthetic amorphous silica: 3%
kaolinite: 13%

The ingredients are blended, hammer-milled until all the solids are essentially under 50 microns, reblended, and packaged.

EXAMPLE 3

Wettable Powder

N-[(4-ethoxy-6-methylamino-1,3,5-triazin-2-yl)-aminocarbonyl]-2-methylsulfonyloxybenzenesulfonamide: 50%
sodium alkylnaphthalenesulfonate: 2%
low viscosity methyl cellulose: 2%
diatomaceous earth: 46%

The ingredients are blended, coarsely hammer-milled and then air-milled to produce particles essentially all below 10 microns in diameter. The product is reblended before packaging.

EXAMPLE 4

Granule

Wettable Powder of Example 3: 5%
attapulgite granules (U.S.S. 20–40 mesh; 0.84–0.42 mm): 95%

A slurry of wettable powder containing ≈25% solids is sprayed on the surface of attapulgite granules while tumbling in a double-cone blender. The granules are dried and packaged.

EXAMPLE 5

Extruded Pellet

2-[[(4-ethoxy-6-methylamino-1,3,5-triazin-2-yl)-aminocarbonyl]aminosulfonyl]benzoic acid, ethyl ester: 25%
anhydrous sodium sulfate: 10%
crude calcium ligninsulfonate: 5%
sodium alkylnaphthalenesulfonate: 1%
calcium/magnesium bentonite: 59%

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 6

Oil Suspension

2-[[(4-ethoxy-6-methylamino-1,3,5-triazin-2-yl)-aminocarbonyl]aminosulfonyl]benzoic acid, methyl ester: 25%
polyoxyethylene sorbitol hexaoleate: 5%
highly aliphatic hydrocarbon oil: 70%

The ingredients are ground together in a sand mill until the solid particles have been reduced to under about 5 microns. The resulting thick suspension may be applied directly, but preferably after being extended with oils or emulsified in water.

EXAMPLE 7

Wettable Powder

2-[[(4-ethoxy-6-methylamino-1,3,5-triazin-2-yl)-aminocarbonyl]aminosulfonyl]benzoic acid, ethyl ester: 20%
sodium alkylnaphthalenesulfonate: 4%
sodium ligninsulfonate: 4%
low viscosity methyl cellulose: 3%
attapulgite: 69%

The ingredients are thoroughly blended. After grinding in a hammer-mill to produce particles essentially all below 100 microns, the material is reblended and sifted through a U.S.S. No. 50 sieve (0.3 mm opening) and packaged.

EXAMPLE 8

Low Strength Granule

N-[(4-ethoxy-6-methylamino-1,3,5-triazin-2-yl)-aminocarbonyl]-2-methylsulfonyloxybenzenesulfonamide: 1%
N,N-dimethylformamide: 9%
attapulgite granules (U.S.S. 20-40 sieve): 90%

The active ingredient is dissolved in the solvent and the solution is sprayed upon dedusted granules in a double cone blender. After spraying of the solution has been completed, the blender is allowed to run for a short period and then the granules are packaged.

EXAMPLE 9

Aqueous Suspension

N-[(4-ethoxy-6-methylamino-1,3,5-triazin-2-yl)-aminocarbonyl]-2-methylsulfonyloxybenzenesulfonamide: 40%
polyacrylic acid thickener: 0.3%
dodecylphenol polyethylene glycol ether: 0.5%
disodium phosphate: 1%
monosodium phosphate: 0.5%
polyvinyl alcohol: 1.0%
water: 56.7%

The ingredients are blended and ground together in a sand mill to produce particles essentially all under 5 microns in size.

EXAMPLE 10

Solution

2-[[(4-ethoxy-6-methylamino-1,3,5-triazin-2-yl)-aminocarbonyl]aminosulfonyl]benzoic acid, ethyl ester, sodium salt: 5%
water: 95%

The salt is added directly to the water with stirring to produce the solution, which may then be packaged for use.

EXAMPLE 11

Low Strength Granule

2-[[(4-ethoxy-6-methylamino-1,3,5-triazin-2-yl)-aminocarbonyl]aminosulfonyl]benzoic acid, methyl ester: 0.1%
attapulgite granules (U.S.S. 20-40 mesh): 99.9%

The active ingredient is dissolved in a solvent and the solution is sprayed upon dedusted granules in a double-cone blender. After spraying of the solution has been completed, the material is warmed to evaporate the solvent. The material is allowed to cool and then packaged.

EXAMPLE 12

Granule

2-[[(4-ethoxy-6-methylamino-1,3,5-triazin-2-yl)-aminocarbonyl]aminosulfonyl]benzoic acid, methyl ester: 80%
wetting agent: 1%
crude ligninsulfonate salt (containing 5-20% of the natural sugars): 10%
attapulgite clay: 9%

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14-100 mesh (1410-149 microns), and packaged for use.

EXAMPLE 13

High Strength Concentrate

2-[[(4-ethoxy-6-methylamino-1,3,5-triazin-2-yl)-aminocarbonyl]aminosulfonyl]benzoic acid, ethyl ester: 99%
silica aerogel: 0.5%
synthetic amorphous silica: 0.5%

The ingredients are blended and ground in a hammer-mill to produce a material essentially all passing a U.S.S. No. 50 screen (0.3 mm opening). The concentrate may be formulated further if necessary.

EXAMPLE 14

Wettable Powder

N-[(4-ethoxy-6-methylamino-1,3,5-triazin-2-yl)-aminocarbonyl]-2-methylsulfonyloxybenzenesulfonamide: 90%
dioctyl sodium sulfosuccinate: 0.1%
synthetic fine silica: 9.9%

The ingredients are blended and ground in a hammer-mill to produce particles essentially all below 100 microns. The material is sifted through a U.S.S. No. 50 screen and then packaged.

EXAMPLE 15

Wettable Powder

2-[[(4-ethoxy-6-methylamino-1,3,5-triazin-2-yl)-aminocarbonyl]aminosulfonyl]benzoic acid, methyl ester: 40%
sodium ligninsulfonate: 20%
montmorillonite clay: 40%

The ingredients are thoroughly blended, coarsely hammer-milled and then air-milled to produce particles essentially all below 10 microns in size. The material is reblended and then packaged.

EXAMPLE 16

Oil Suspension

2-[[(4-ethoxy-6-methylamino-1,3,5-triazin-2-yl)-aminocarbonyl]aminosulfonyl]benzoic acid, ethyl ester: 35% blend of polyalcohol carboxylic esters and oil soluble petroleum sulfonates: 6% xylene: 59%

The ingredients are combined and ground together in a sand mill to produce particles essentially all below 5 microns. The product can be used directly, extended with oils, or emulsified in water.

EXAMPLE 17

Dust

N-[(4-ethoxy-6-methylamino-1,3,5-triazin-2-yl)-aminocarbonyl]-2-methylsulfonyloxybenzenesulfonamide: 10% attapulgite: 10%

Pyrophyllite: 80%

The active ingredient is blended with attapulgite and then passed through a hammer-mill to produce particles substantially all below 200 microns. The ground concentrate is then blended with powdered pyrophyllite until homogeneous.

Utility

Quite surprisingly, in view of the known properties of generically related compounds, the compounds of the present invention are potent herbicides, specifically useful for selective, post-emergence and pre-emergence, grass and broadleaf weed control in rape (*Brassica napus*).

The rates of application for the compounds of the invention are determined by a number of factors. These include: crop species involved, types of weeds to be controlled, weather and climate, formulations selected, mode of application, amount of foliage present, etc. In general terms, the subject compounds should be applied at levels of from 0.001 to 5 kg/ha, preferably 0.004 to 0.125 kg/ha.

The compounds of this invention may be used in combination with other commercial herbicides. They are particularly useful in combination with the following herbicides:

| Common Name | Chemical Name |
|---|---|
| alloxydim-sodium | Sodium salt of 2-(1-allyl-oxy-aminobutylidene)-5,5-dimethyl-4-methoxycarbonylcyclohexane-1,3-dione |
| carbetamide | N—ethyl-2-[[(phenylamino)carbonyl]oxy]propanamide (R)-isomer |
| dalapon | 2,2-dichloropropionic acid |
| diallate | s-(2,3-Dichloroallyl)diisopropylthiocarbamate |
| diclofop methyl | Methyl 2-[4-(2',4'-dichlorophenoxy)phenoxy]propanate |
| diuron | 3-(3,4-dichlorophenyl)-1,1-dimethylurea |
| fluazifop-butyl | (±)-butyl 2-[4-[(5-(trifluoromethyl)-2-pyridinyl)oxy]-phenoxy]propanoate |
| haloxyfop-methyl | Methyl 2-(4-((3-chloro-5-(trifluoromethyl)-2-pyridinyl)oxy)-phenoxy)propanoate |
| methazachlor | 2-chloro-N—(2,6-dimethylphenyl)-N—(1H—pyrazol-1-yl methyl)acetamide |
| napropamide | 2-(α-Naphthoxy)-N,N—diethyl propionamide |
| nitralin | 4-methylsulfonyl-2,6-dinitro-N,N—dipropylaniline |
| propyzamide | 3,5-dichloro(N—1,1-dimethyl)-2-propynyl)benzamide |
| sethoxydim | 2-[1-(ethoxyimino)butyl]-5-[2-(ethylthio)propyl]-3-hydroxy- |

| Common Name | Chemical Name |
|---|---|
| | 2-cyclohexen-1-one |
| TCA | trichloroacetic acid |
| 3,6-dichloro-picolinic acid | 3,6-Dichloro-2-pyridinecarboxylic acid |
| trifluralin | α,α,α-Trifluoro-2,6-dinitro-N,N—dipropyl-p-toluidine |

The selective herbicidal properties of the subject compounds that make them useful as rape herbicides were discovered in a number of greenhouse tests, conducted as described below.

Compounds

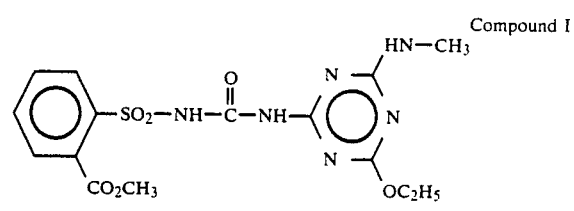

Compound I

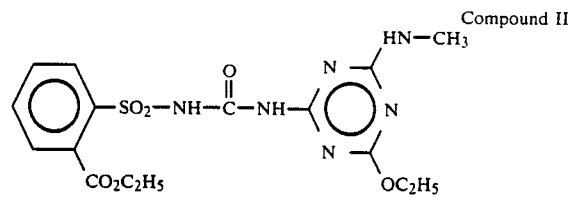

Compound II

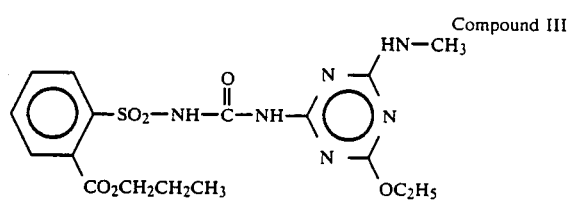

Compound III

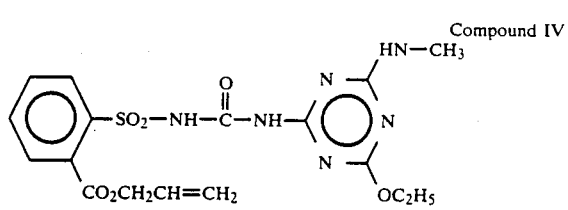

Compound IV

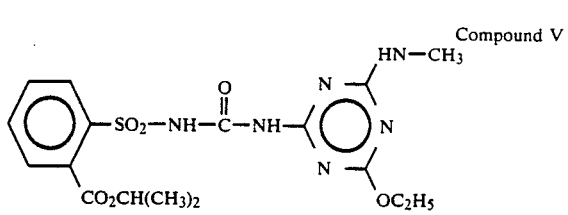

Compound V

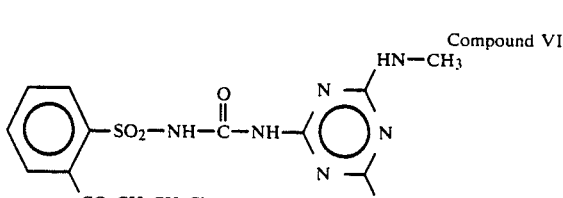

Compound VI

-continued
Compounds

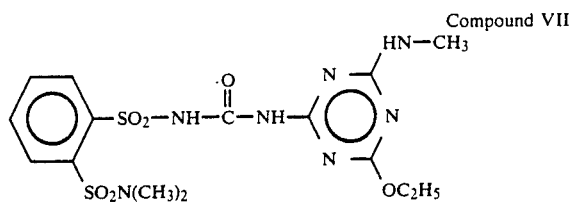

Compound VII weed species, along with cotton and bushbean, were treated with a soil/foliage application. At the time of treatment, the plants ranged in height from 2 to 18 cm. Treated plants and controls were maintained in a greenhouse for sixteen days, after which all species were compared to controls and visually rated for response to treatment. The ratings, summarized in Table A, are based on a numerical scale extending from 0=no injury, to 10=complete kill. The accompanying descriptive symbols have the following meanings:

TABLE A

| | Compound Number | | | | | | | |
|---|---|---|---|---|---|---|---|---|
| | I | II | III | IV | V | VI | VII | VIII |
| | PRE-EMERGENCE | | | | | | | |
| Rate kg/ha | | | | 0.05 | | | | |
| Bushbean | — | — | — | — | — | — | — | — |
| Cotton | — | — | — | — | — | — | — | — |
| Sorghum | 5C,9H | 4C,9H | 2C,8G | 3C,8H | 3C,9H | 2C,9G | 2C,9G | 5C,9H |
| Corn | 3C,9G | 5C,9H | 2C,7G | 2C,8H | 2C,9G | 2C,9G | 2C,9G | 3C,9H |
| Soybean | 3C,8H | 3C,6H | 3C,3G | 0 | 2C,8G | 2C,6H | 2C,2H | 2C,8H |
| Wheat | 2C,8G | 2C,6G | 0 | 2G | 2G | 1C | 2C,9G | 4C,9H |
| Wild Oats | 5C,9G | 3C,9G | 3C,8H | 2C,8G | 3C,9G | 2C,9H | 2C,9G | 5C,9H |
| Rice | 10H | 10E | 3C,8G | 3C,8H | 10E | 9H | 10E | 10E |
| Barnyardgrass | 5C,9H | 3C,9H | 3C,6H | 3C,4H | 5C,9H | 2C,9H | 2C,9H | 9H |
| Crabgrass | 3C,7G | 1C,5G | 0 | 1C | 3G | 2G | 2C,8G | 2C,8G |
| Morningglory | 9C | 9G | 3C,8H | 8H | 9G | 9G | 9C | 9H |
| Cocklebur | 8H | 9H | 9H | 8H | 9H | 8H | 9H | 9H |
| Cassia | 3C,9G | 5C,9G | 2C,5G | 8G | 5C,9G | 2C,4G | 9G | 5C,9G |
| Nutsedge | 10E | 10E | 0 | 9G,3C | 9G | 8G | 4G | 6G |
| Sugar beets | 9C | 10E | 3C,9G | 9C | 10E | 4C,9G | 10E | 10E |
| | Compound Number | | | | | | | |
| | I | II | III | IV | V | VI | VII | VIII |
| | POST-EMERGENCE | | | | | | | |
| Rate kg/ha | | | | 0.05 | | | | |
| Bushbean | 4C,8G,6Y | 5C,7G,6G | 4C,7G,6G | 3C,5G,6Y | 3C,7G,6Y | 3C,7G,6Y | 1C,1H | 4C,8G,6Y |
| Cotton | 4C,9G | 5C,9G | 4C,4H,8G | 3C,3H,8G | 4C,9G | 3C,3H,9G | 3C,6H | 4C,9G |
| Sorghum | 2C,9G | 3U,9G | 3C,8H | 4C,9H | 9G | 3C,9H | 2C,9G | 3C,9G |
| Corn | 5C,9G | 3U,9G | 2C,4G | 1C,5G | 3C,8H | 2C,5H | 3C,9G | 3C,9H |
| Soybean | 5C,9G | 3C,9G | 3C,9G | 1C,6G | 3C,9G | 4C,9G | 3C,3H | 4C,9G |
| Wheat | 7G | 5G | 0 | 0 | 0 | 0 | 7G | 4G |
| Wild Oats | 5C,9G | 3C,9G | 1C | 2C | 4C,9H | 1C,5G | 2C,9H | 3C,9G |
| Rice | 5C,9G | 5C,9G | 2C,9H | 5C,9G | 6C,9G | 4C,9G | 5C,9G | 5C,9G |
| Barnyardgrass | 9C | 9C | 3C,8H | 2C,8H | 2C,9H | 9H | 3C,9H | 5C,9H |
| Crabgrass | 2C,9G | 2C,9G | 0 | 1C,3G | 7G | 4G | 3C,9G | 2C,9G |
| Morningglory | 4C,8G | 5C,9G | 3C,8H | 3C,8H | 5C,9G | 3C,8H | 3C,9G | 4C,9G |
| Cocklebur | 1C,6G | 5C,9G | 4C,9G | 3C,9H | 6C,9G | 3C,9G | 2C,9H | 7G |
| Cassia | 9C | 5C,9G | 3C,5H | 3C,8H | 6C,9G | 3C,9G | 3C,9H | 5C,9G |
| Nutsedge | 2C,9G | 9G | 0 | 2G | 2C,9G | 5G | 5G | 0 |
| Sugar beets | 9C | 9C | 9C | 9C | 9C | 9C | 9C | 2C,3G |

C = chlorosis/necrosis;
E = emergence inhibition;
G = growth retardation;
H = formative effect; and
6Y = abscised buds or flowers.

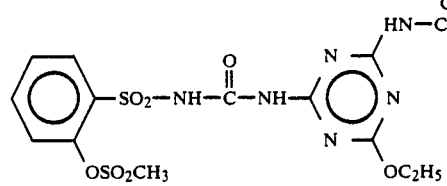

Compound VIII

Test A

Seeds of crabgrass (Digitaria spp.), barnyardgrass (Echinochloa crusgalli), wild oats (Avena fatua), sicklepod (Cassia obtusifolia), morningglory (Ipomoea spp.), cocklebur (Xanthium pensylvanicum), sorghum, corn, soybean, sugar beet, rice, wheat, and purple nutsedge (Cyperus rotundus) tubers were planted and treated pre-emergence with the test chemicals dissolved in a non-phytotoxic solvent. At the same time, these crop and

Test B

Two plastic pans lined with polyethylene liners were filled with prepared soil. One pan was planted with seeds of wheat (Triticum aestivum), barley (Hordeum vulgare), wild oats (Avena fatua), cheatgrass (Bromus secalinus), blackgrass (Alopecurus myosuroides), annual bluegrass (Poa annua), green foxtail (Setaria viridis), Italian ryegrass (Lolium multiflorum) and rape (Brassica napus). The other pan was planted with seeds of Russian thistle (Salsola kali), cleavers (Galium aparine), speedwell (Veronica persica), kochia (Kochia scoparia), shepherdspurse (Capsella bursa-pastoris), Matricaria inodora, black nightshade (Solanum nigrum), wild buckwheat (Polygonum convolvulus) and sugar beets (Beta vulgaris). The above two pans were treated pre-emergence. At the same time, two pans in which the above plant species were already growing were treated post-emergence. Plant heights at the time of treatment ranged from 1–20 cm depending on plant species.

The compounds applied were diluted with a non-phytotoxic solvent and sprayed over-the-top of the pans. An untreated control and a solvent alone control were included for comparison. All treatments were maintained in the greenhouse for 19–22 days at which time the treatments were compared to the controls and the effects visually rated. The recorded data are presented in Table B.

The following rating system was used:

TABLE B

| | Compound Number | | | | | | | | | | | | |
|---|---|---|---|---|---|---|---|---|---|---|---|---|---|
| | I | | | | II | | | | | | | | V |
| | | | | | Run I | | | | Run II | | | | Run I |
| | PRE-EMERGENCE | | | | | | | | | | | | |
| Rate kg/ha | 0.06 | 0.015 | 0.004 | 0.0009 | 0.06 | 0.015 | 0.004 | 0.0009 | 0.06 | 0.015 | 0.004 | 0.0009 | 0.06 |
| Rape | 8G,3C | 1G | 1G | 0 | 5G | 0 | 0 | 0 | 0 | 0 | 0 | | 5G |
| Italian Ryegrass | 9G,9C | 7G,4C | 3G | 0 | 10C | 9G,9C | 5G | 2G | 5G,2C | 4G | 7G | | 8G |
| Green Foxtail | 5G,4C | 5G,5C | 0 | 0 | 2G | 0 | 0 | 0 | 1G | 0 | 0 | | 0 |
| Annual Bluegrass | 9G,9C | 9G,7C | 4G | 0 | 9G,9C | 8G,8C | 4G | 1G | 9G,3C | 9G,2C | 5G | | 8G |
| Blackgrass | 9G,9C | 8G,9C | 7G | 1G | 9G,9C | 9G,9C | 8G | 4G | 9G,4C | 9G,3C | 7G | | 9G,4C |
| Cheatgrass | 9G,5C | 9G,2C | 8G | 5G | 9G,9C | 9G,9C | 8G | 4G | 8G,3C | 7G,5C | 7G | | 7G,5C |
| Wild Oats | 7G | 6G | 3G | 2G | 10G | 10G | 9G,4C | 4G | 8G | 8G,2C | 8G,7C | | 7G,3C |
| Barley | 6G | 4G | 5G | 1G | 1G | 1G | 0 | 5G | 5G | 5G | 6G | | 2G |
| Wheat | 5G | 3G | 5G | 1G | 0 | 0 | 0 | 0 | 2G | 2G | 1G | | 0 |
| Matricaria inodora | 10C | 9G | 9G | 7G | 10C | 10C | 10C | 6G | 9G | 8G | 9G,7C | | 9G |
| Galium aparine | 10C | 9G,7C | 6G | 4G | 10C | 10C | 10C | 10C | 9G,9C | 9G,9C | 10C | | 9G,9C |
| Russian thistle | 10C | 5G,4C | 7G | 0 | 10C | 10C | 4G | 0 | 4G | 5G | 4G | | 6G |
| Shepherdspurse | 10C | 10C | 10C | 7G | 10C | 10C | 5G | 1G | 10C | 10C | 8G | | 10C |
| Kochia | 9G,4C | 9G,3C | 7G | 1G | 9G,9C | 8G,8C | 0 | 0 | 9G | 9G | 7G | | 9G |
| Black Nightshade | 9G,7C | 9G,4C | 6G | 2G,1C | 8G | 7G | 0 | 0 | 4G | 5G | 3G | | 9G,9C |
| Speedwell | 8G,3C | 8G | 8G | 8G | 8G | 7G | 0 | 2G | 10C | 10C | 9G | | 10C |
| Wild Buckwheat | 7G,2C | 5G | 6G,3C | 0 | 9G | 7G | 0 | 0 | 5G | 5G | 1G,1C | | 9G,9C |
| Sugar beets | 9G,9C | 9G,9C | 9G | 3G | 10C | 10C | 7G | 9G | 9G,9C | 8G,8C | 9G,9C | | 9G,9C |

| | Compound Number | | | | | | | | | |
|---|---|---|---|---|---|---|---|---|---|---|
| | V | | | | | | | VI | | VIII |
| | Run I | | | Run II | | | | | | |
| | PRE-EMERGENCE | | | | | | | | | |
| Rate kg/ha | 0.015 | 0.004 | 0.0009 | 0.06 | 0.015 | 0.004 | 0.0009 | 0.06 | 0.015 | 0.06 | 0.015 |
| Rape | 1G | 0 | 0 | 1C | 0 | 0 | 0 | — | 0 | 0 | 0 |
| Italian Ryegrass | 5G | 0 | 0 | 8G,1C | 2G | 0 | 0 | 9G | 7G | 9G,4C | 5G |
| Green Foxtail | 0 | 2G | 0 | 0 | 0 | 0 | 0 | 9G,9C | 8C,9G | 8G | 0 |
| Annual Bluegrass | 6G | 6G | 2G | 9G,9C | 8G | 0 | 0 | 8G | 7G | 9G,8C | 6G |
| Blackgrass | 7G | 5G | 3G | 9G,9C | 8G | 4G | 0 | 9G | 6G | 9G,7C | 8G |
| Cheatgrass | 4G | 3G | 0 | 2G | 0 | 0 | 0 | 8G | 6G | 8G | 7G |
| Wild Oats | 4G | 2G | 0 | 9G | 7G | 0 | 0 | 4G | 0 | 7G | 3G |
| Barley | 3G | 3G | 1G | 7G | 5G | 0 | 0 | 3G | 0 | 2G | 1G |
| Wheat | 0 | 3G | 1G | 3G | 3G | 0 | 0 | 2G | 0 | 2G | 1G |
| Matricaria inodora | 9G | 5G | 0 | 8G,7C | 8G,7C | 8G | 0 | 8G | 3G | 9G | 9G |
| Galium aparine | 9G,9C | 8G | 7G | 9G,9C | 9G,9C | 0 | 0 | 9G | 2G | 8G,9C | 8G,7C |
| Russian thistle | 2G | 5G | 0 | 4G | 2G | 3G | 0 | 0 | 0 | 10C | 4G |
| Shepherdspurse | 10C | 8G | 2G | 10C | 10C | 4G | 0 | 9G | 4G | 9G | 3G |
| Kochia | 7G | 6G | 2G | 9G,8C | 9G,8C | 4G | 0 | 8G,3C | 7G | 8G | 0 |
| Black Nightshade | 9G | 5G | 0 | 10C | 10C | 3G | 0 | 9G,5C | 0 | 9G,7C | 2G |
| Speedwell | 10C | 7G,1C | 0 | 10C | 10C | 8G | 0 | 0 | 0 | 8G | 0 |
| Wild Buckwheat | 8G,7C | 6G | 2G | 8G,9G | 9G,8C | 3G | 0 | 0 | 0 | 7G | 2G |
| Sugar beets | 8G,2C | 8G,8C | 8G,7C | 8G,9C | 9G,7C | 4G,1C | 0 | 7G | 4G | 8G,4C | 3G |

| | Compound Number | | | | | | | | | | | | |
|---|---|---|---|---|---|---|---|---|---|---|---|---|---|
| | I | | | | II | | | | | | | | V |
| | | | | | Run I | | | | Run II | | | | Run I |
| | POST-EMERGENCE | | | | | | | | | | | | |
| Rate kg/ha | 0.06 | 0.015 | 0.004 | 0.0009 | 0.06 | 0.015 | 0.004 | 0.0009 | 0.06 | 0.015 | 0.004 | 0.009 | 0.06 |
| Rape | — | 1G | 0 | 0 | 3G | 0 | 0 | 1C | 0 | 0 | 0 | | 0 |
| Italian Ryegrass | 10C | 7G,3C | 7G | 0 | 10C | 9G | 4G | 1G | 9G,9C | 8G,2C | 4G | | 5G |
| Green Foxtail | 10C | 3C,4G | 0 | 0 | 4G | 0 | 0 | 0 | 2G | 1G | 0 | | 0 |
| Annual Bluegrass | 10C | 7G,2C | 2G | 0 | 10C | 8G | 3G | 0 | 9G,9C | 8G,4C | 5G | | 4G |
| Blackgrass | 10C | 9G,7C | 7G | 0 | 10C | 10C | 3G | 1G | 9G,9C | 8G,7C | 7G | | 5G |
| Cheatgrass | 9G,9C | 9G,5C | 8G | 2G | 7G,7C | 5G | 2G | 1G | 9G,9C | 9G,3C | 7G | | 7G |
| Wild Oats | 8G | 6G | 3G | 0 | 8G | 8G | 4G | 1G | 4G | 4G | 4G | | 8G,2C |
| Barley | 8G | 2G | 4G | 0 | 3G | 1G | 0 | 2G | 3G | 3G | 5G | | 0 |
| Wheat | 8G | 3G | 1G | 0 | 2G | 2G | 0 | 0 | 4G | 4G | 0 | | 0 |
| Matricaria inodora | 10C | 9G,5C | 6G,1C | 4G,1C | 9G | 7G | 0 | 4G | 10C | 8G,7C | 8C | | 4G,7C |
| Galium aparine | 10C | 10C | 10C | 10C | 10C | 9G,7C | 2G | 8G | 10C | 10C | 10C | | 10C |
| Russian thistle | 10C | 10C | 10C | 8G | 10C | 5G | 0 | 9G | 10C | 8G,4C | 10C | | 10C |
| Shepherdspurse | 10C | 10C | 8G | 5G | 8G | 7G | 0 | 8G | 10C | 10C | 10C | | 10C |
| Kochia | 9G,9C | 9G,8C | 8G,4C | 7G | 10C | 9G | 0 | 8G,7C | 10C | 9G,3C | 8G,8C | | 4G |
| Black Nightshade | 10C | 10C | 8G,7C | 1G | 7G | 4G | 0 | 0 | 10C | 5G | 6G,2C | | 10C |
| Speedwell | 10C | 5G,7C | 3G | 3G | 5G | 3G | 0 | 1G | 9G,9C | 6G | 7G | | 8G |
| Wild Buckwheat | 10C | 10C | 6G,3C | 6G | 9G | 4G | 0 | 1G,1C | 10C | 7G | 6G | | 8G |
| Sugar beets | 9G,9C | 9G,7C | 10C | 4G,1C | 10C | 10C | 4G | 8G,7C | 10C | 10C | 10C | | 10C |

TABLE B-continued

| | Compound Number | | | | | | | | | | |
|---|---|---|---|---|---|---|---|---|---|---|---|
| | V | | | | | | | VI | | VIII | |
| | Run I | | | Run II | | | | | | | |
| | POST-EMERGENCE | | | | | | | | | | |
| Rate kg/ha | 0.015 | 0.004 | 0.0009 | 0.06 | 0.015 | 0.004 | 0.0009 | 0.06 | 0.015 | 0.06 | 0.015 |
| Rape | 0 | 5G,4C | 1G,1C | 1C | 0 | 3G | 0 | 0 | 0 | 0 | 0 |
| Italian Ryegrass | 2G | 0 | 0 | 10C | 5G | 0 | 0 | 9G | 5G | 10C | 4G |
| Green Foxtail | 0 | 0 | 0 | 10C | 7G | 0 | 0 | 7G,3C | 4G,3C | 7G,8C | 3G,1C |
| Annual Bluegrass | 2G | 1G | 0 | 10C | 7G | 0 | 0 | 7G | 5G | 8G | 2G |
| Blackgrass | 3G | 6G | 1G | 10C | 7G | 0 | 0 | 10C | 10C | 10C | 6G |
| Cheatgrass | 2G | 4G | 0 | 8G | 6G | 0 | 0 | 8G | 5G | 8G | 3G |
| Wild Oats | 4G | 1G,1C | 0 | 8G | 5G | 0 | 0 | 9G | 8G,7C | 9G | 5G |
| Barley | 0 | 1G | 0 | 3G | 1G | 0 | 0 | 7G,3C | 4G | 5G | 1G |
| Wheat | 0 | 2G | 0 | 5G | 2G | 0 | 0 | 5G,4C | 4G | 5G | 1G |
| *Matricaria inodora* | 2G,4C | 5G | 0 | 10C | 8G,8C | 5G | 0 | 4G | 0 | 3G | 0 |
| *Galium aparine* | 3G,3C | 7G | 3G | 10C | 10C | 8G | 0 | 7G,7C | 7G | 5G,4C | 1G,1C |
| Russian thistle | 8G | 8G | 2G | 10C | 10C | 0 | 0 | 5G | 0 | 7G | 3G |
| Shepherdspurse | 6G | 7G | 0 | 10C | 10C | 4G | 3G | 7G | 0 | 7G | 2G |
| Kochia | 1G | 0 | 0 | 9G,9C | 4G,2C | 0 | 0 | 5G,5C | 0 | 5G,4C | 0 |
| Black Nightshade | 8G | 4G | 0 | 9G,9C | 8G,6C | 0 | 0 | 9G | 5G,3C | 8G | 4G |
| Speedwell | 3G | 7G | 5G | 9G,5C | 8G,7C | 3G | 0 | 0 | 0 | 5G | 0 |
| Wild Buckwheat | 7G,1C | 7G | 4G | 10C | 10C | 4G,1C | 0 | 1G,1C | 0 | 6G,3C | 0 |
| Sugar beets | 10C | 4G,7C | 5G | 10G | 8G,7C | 5G,3C | 0 | 10C | 4G,3C | 7G,2C | 6G |

0 = no effect;
10 = maximum effect;
C = chlorosis or necrosis; and
G = growth retardation.

Test C

The object of this test was to evaluate compounds for post-emergence and pre-emergence weed control in rape.

Two plastic pans lined with polyethylene liners were filled with prepared Sassafras loamy sand soil. One pan was planted with seeds of *Galium aparine*, Veronica (*Veronica persica*), *Matricaria inodora*, common lambsquarters (*Chenopodium album*), wild buckwheat (*Polygonum convolvulus*), wild mustard (*Brassica kaber*), redroot pigweed (*Amaranthus retroflexus*), chickweed (*Stellaria media*) and rape (*Brassica napus*). The other pan was planted with seeds of Italian ryegrass (*Lolium multiflorum*), green foxtail (*Setaria viridis*), wild oats (*Avena fatua*), wheat (*Triticum aestivum*), barley (*Hordeum vulgare*), sunflower (*Helianthus annuus*), soybean (*Glycine max*), blackgrass (*Alopecurus myosuroides*) and rape (*Brassica napus*). The above two pans were treated pre-emergence. Two pans in which the above plant species were already growing were treated post-emergence. Plant heights at the time of treatment ranged from 1–20 cm depending on plant species.

The compounds applied were diluted with a non-phytotoxic solvent and sprayed over-the-top of the pans. An untreated control and a solvent alone control were included for comparison. All treatments were maintained in the greenhouse for 19–22 days at which time the treatments were compared to the controls and the effects visually rated. The recorded data are presented in Table C.

The following rating system was used:

TABLE C

PRE-EMERGENCE

| | \multicolumn{3}{c|}{Compound Number} | | | | | | | | | | | | | | | | | | | | | |
|---|---|---|---|---|---|---|---|---|---|---|---|---|---|---|---|---|---|---|---|---|---|---|---|
| | I | | | II | | | III | | | IV | | | V | | | VI | | | VII | | | VIII | | |
| Rate kg/ha | 0.125 | 0.06 | 0.015 | 0.125 | 0.06 | 0.015 | 0.125 | 0.06 | 0.015 | 0.125 | 0.06 | 0.015 | 0.125 | 0.06 | 0.015 | 0.125 | 0.06 | 0.015 | 0.125 | 0.06 | 0.015 | 0.125 | 0.06 | 0.015 |
| *Galium aparine* | — | — | — | — | — | — | — | — | — | — | — | — | — | — | — | — | — | — | — | — | — | — | — | — |
| Veronica | 100 | 100 | 90 | 100 | 100 | 30 | 100 | 100 | 80 | 100 | 80 | 60 | 10 | 95 | 95 | 80 | 100 | 40 | 0 | 80 | 70 | 30 | 100 | 80 | 0 |
| *Matricaria inodora* | 100 | 90 | 80 | 100 | 100 | 40 | 100 | 100 | 90 | 100 | 80 | 70 | 30 | 10 | 80 | 75 | 100 | 70 | 0 | 100 | 80 | 10 | 100 | 100 | 80 |
| Common Lambsquarters | 100 | 100 | 100 | 100 | 100 | 90 | 100 | 100 | 100 | 100 | 100 | 60 | 0 | 10 | 100 | 100 | 0 | 0 | 0 | 100 | 20 | 30 | 100 | 100 | 95 |
| Wild Buckwheat | 95 | 90 | 90 | 100 | 100 | 60 | 95 | 95 | 60 | 70 | 30 | 0 | 0 | 45 | 70 | 60 | 0 | 0 | 0 | 20 | 0 | 10 | 0 | 0 | 0 |
| Wild Mustard | 100 | 100 | 100 | 100 | 100 | 95 | 100 | 100 | 70 | 90 | 100 | 0 | 100 | 100 | 100 | 95 | 0 | 30 | 80 | 95 | 100 | 80 | 95 | 95 | 80 |
| Pigweed | 100 | 100 | 100 | 100 | 90 | 90 | 90 | 85 | 85 | 100 | 90 | 0 | 100 | 100 | 95 | 100 | 0 | 70 | 10 | 100 | 20 | 60 | 90 | 90 | 30 |
| Chickweed | 100 | 100 | 80 | 100 | 100 | 80 | 95 | 95 | 60 | 60 | 10 | 0 | 100 | 95 | 20 | 80 | 0 | 10 | 0 | 20 | 95 | 100 | 100 | 100 | 75 |
| Rape-Pot 1 | 10 | 0 | 0 | 0 | 10 | 0 | 0 | 0 | 0 | 0 | 0 | 0 | 0 | 0 | 0 | 0 | 0 | 0 | 0 | 80 | 10 | 10 | 10 | 0 | 100 |
| Italian Ryegrass | 100 | 100 | 85 | 90 | 90 | 20 | 60 | 0 | 0 | 10 | 0 | 0 | 10 | 10 | 0 | 10 | 40 | 0 | 0 | 95 | 0 | 10 | 100 | 95 | 0 |
| Green Foxtail | 100 | 100 | 30 | 70 | 30 | 0 | 0 | 0 | 0 | 0 | 0 | 0 | 0 | 0 | 0 | 0 | 40 | 40 | 0 | 95 | 80 | 30 | 100 | 90 | 80 |
| Wild Oats | 100 | 100 | 90 | 85 | 80 | 70 | 0 | 0 | 0 | 0 | 0 | 0 | 80 | 70 | 10 | 0 | 40 | 40 | 0 | 80 | 60 | 0 | 80 | 80 | 80 |
| Wheat | 30 | 95 | 0 | 60 | 10 | 0 | 0 | 0 | 0 | 0 | 0 | 0 | 10 | 0 | 0 | 0 | 40 | 40 | 0 | 20 | 30 | 0 | 0 | 0 | 0 |
| Barley | 60 | 30 | 0 | 60 | 20 | 0 | 85 | 0 | 0 | 0 | 0 | 0 | 0 | 0 | 0 | 0 | 40 | 40 | 0 | 30 | 0 | 0 | 80 | 80 | 40 |
| Sunflower | 95 | 85 | 40 | 95 | 95 | 90 | 10 | 0 | 0 | 0 | 0 | 0 | 40 | 40 | 20 | 20 | 40 | 40 | 0 | 80 | 0 | 0 | 60 | 60 | 40 |
| Soybean | 95 | 90 | 10 | 90 | 80 | 0 | 80 | 10 | 0 | 40 | 0 | 0 | 10 | 10 | 20 | 0 | 40 | 40 | 0 | 60 | 80 | 0 | 60 | 95 | 40 |
| Blackgrass | 100 | 100 | 100 | 100 | 100 | 35 | 95 | 80 | 70 | 80 | 70 | 10 | 100 | 60 | 90 | 60 | 0 | 10 | 0 | 100 | 0 | 0 | 95 | 95 | 80 |
| Rape Pot 2 | 20 | 0 | 0 | 0 | 0 | 0 | 0 | 0 | 0 | 0 | 10 | 0 | 0 | 0 | 0 | 0 | 0 | 0 | 0 | 0 | 0 | 0 | 0 | 0 |

POST-EMERGENCE

| | \multicolumn{3}{c|}{Compound Number} | | | | | | | | | | | | | | | | | | | | | |
|---|---|---|---|---|---|---|---|---|---|---|---|---|---|---|---|---|---|---|---|---|---|---|---|
| | I | | | II | | | III | | | IV | | | V | | | VI | | | VII | | | VIII | | |
| Rate kg/ha | 0.125 | 0.06 | 0.015 | 0.125 | 0.06 | 0.015 | 0.125 | 0.06 | 0.015 | 0.125 | 0.06 | 0.015 | 0.125 | 0.06 | 0.015 | 0.125 | 0.06 | 0.015 | 0.125 | 0.06 | 0.015 | 0.125 | 0.06 | 0.015 |
| *Galium aparine* | 90 | 90 | 10 | — | — | — | — | — | — | 0 | 0 | 0 | 100 | 100 | 40 | 70 | 70 | 0 | 0 | 0 | 0 | 60 | 30 | 80 |
| Veronica | 95 | 80 | 30 | 30 | 40 | 20 | 0 | 10 | 0 | 10 | 10 | 0 | 80 | 60 | 90 | 50 | 50 | 55 | 85 | 10 | 20 | 70 | 10 | 60 |
| *Matricaria inodora* | 100 | 100 | 100 | 90 | 90 | 90 | 80 | 80 | 20 | 100 | 90 | 70 | 100 | 100 | 0 | 100 | 100 | 60 | 60 | 40 | 100 | 100 | 85 | 85 |
| Common Lambsquarters | 100 | 100 | 85 | 60 | 60 | 30 | 0 | 0 | 0 | 60 | 40 | 0 | 70 | 20 | 70 | 30 | 30 | 60 | 45 | 0 | 0 | 85 | 0 | 0 |
| Wild Buckwheat | 100 | 100 | 70 | 60 | 60 | 30 | 20 | 20 | 0 | 100 | 90 | 0 | 95 | 100 | 85 | 100 | 100 | 90 | 50 | 50 | 50 | 100 | 100 | 100 |
| Wild Mustard | 100 | 100 | 100 | 100 | 100 | 100 | 80 | 80 | 50 | 100 | 40 | 0 | 100 | 100 | 10 | 30 | 30 | 20 | 0 | 0 | 70 | 100 | 100 | 80 |
| Pigweed | 100 | 100 | 80 | 100 | 60 | 20 | 0 | 0 | 0 | 50 | 50 | 0 | 40 | 80 | 30 | 0 | 0 | 0 | 10 | 0 | 0 | 70 | 60 | 0 |
| Chickweed | 100 | 100 | 100 | 90 | 90 | 60 | 0 | 0 | 0 | 60 | 0 | 0 | 95 | 50 | 0 | 100 | 30 | 0 | 0 | 60 | 70 | 0 | 0 | 0 |
| Rape-Pot 1 | 0 | 95 | 0 | 0 | 0 | 0 | 0 | 0 | 0 | 0 | 0 | 0 | 30 | 0 | 70 | 0 | 10 | 0 | 0 | 75 | 10 | 10 | 0 | 75 |
| Italian Ryegrass | 100 | 100 | 100 | 100 | 35 | 70 | 80 | 80 | 0 | 0 | 0 | 0 | 60 | 50 | 0 | 100 | 100 | 0 | 100 | 60 | 60 | 70 | 70 | 90 |
| Green Foxtail | 100 | 90 | 50 | 90 | 10 | 0 | 10 | 10 | 0 | 0 | 0 | 0 | 10 | 75 | 30 | 100 | 100 | 0 | 100 | 75 | 75 | 70 | 70 | 20 |
| Wild Oats | 100 | 100 | 95 | 100 | 20 | 20 | 0 | 0 | 0 | 80 | 0 | 0 | 85 | 0 | 70 | 70 | 60 | 0 | 70 | 60 | 60 | 90 | 30 | 80 |
| Wheat | 50 | 20 | 20 | 60 | 20 | 0 | 0 | 0 | 0 | 0 | 0 | 0 | 0 | 0 | 0 | 20 | 20 | 40 | 20 | 20 | 0 | 20 | 20 | 20 |
| Barley | 70 | 60 | 30 | 100 | 30 | 0 | 0 | 0 | 0 | 0 | 0 | 0 | 30 | 75 | 60 | 50 | 50 | 10 | 50 | 50 | 0 | 10 | 10 | 10 |
| Sunflower | 50 | 20 | 0 | 80 | 75 | 80 | 80 | 80 | 0 | 90 | 90 | 0 | 100 | 0 | 10 | 60 | 0 | 40 | 70 | 70 | 30 | 80 | 80 | 30 |
| Soybean | 60 | 40 | 35 | 60 | 60 | 30 | 10 | 10 | 0 | 80 | 80 | 0 | 70 | 60 | 80 | 30 | 30 | 10 | 10 | 0 | 0 | 45 | 45 | 80 |
| Rape-Pot 2 | 0 | 0 | 0 | 0 | 0 | 20 | 0 | 0 | 0 | 0 | 0 | 0 | — | 0 | 65 | 0 | 0 | 0 | 0 | 0 | 0 | 0 | 0 | 0 |

0 = no effect; and
100 = complete kill.

Test D

The object of this test was to further evaluate compounds which had shown utility for post-emergence weed control in rape in Tests A or B. Cultivars of rape and wild mustard, a broadleaf weed, were sprayed post-emergence in a non-phytotoxic solvent and rated for plant response 21 days later. The rating system was the same as used for Test C. Data are presented in Table D.

Plant species were seeded in prepared Sassafras loamy sand soil contained in 12.5 cm diameter plastic pots and grown in a greenhouse. The rape and wild mustard was 14 days old when sprayed.

Note that compounds I and II are particularly useful for the post-emergence control of wild mustard in rape. Wild mustard is a common problem weed when growing rape.

TABLE D

| Rate kg/ha | 0.06 | 0.015 |
|---|---|---|
| | POST-EMERGENCE | |
| Compound Number I | | |
| Cultivars | | |
| 'Regent' rape | 10 | 0 |
| 'Altex' rape | 10 | 0 |
| 'Andor' rape | 0 | 0 |
| 'Westar' rape | 10 | 0 |
| Wild Mustard | 95 | 95 |
| Compound Number II | | |
| Cultivars | | |
| 'Regent' rape | 0 | 0 |
| 'Altex' rape | 10 | 0 |
| 'Andor' rape | 0 | 0 |
| 'Westar' rape | 0 | 0 |
| Wild Mustard | 100 | 80 |

What is claimed is:

1. A compound of the formula

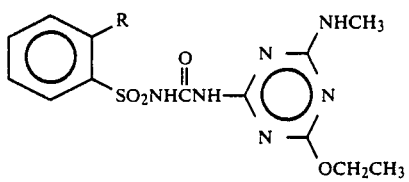

wherein

R is $CO_2CH_3$, $CO_2CH_2CH_3$, or $OSO_2CH_3$.

2. The compound of claim 1 which is 2-[[(4-ethoxy-6-methylamino-1,3,5-triazin-2-yl)aminocarbonyl]aminosulfonyl]benzoic acid, methyl ester.

3. The compound of claim 1 which is 2-[[(4-ethoxy-6-methylamino-1,3,5-triazin-2-yl)aminocarbonyl]aminosulfonyl]benzoic acid, ethyl ester.

4. The compound of claim 1 which is N-[(4-ethoxy-6-methylamino-1,3,5-triazin-2-yl)aminocarbonyl]-2-methylsulfonyloxybenzenesulfonamide.

5. A composition suitable for controlling the growth of undesired vegetation which comprises an effective amount of a compound of claim 1 and at least one of the following: surfactant, solid or liquid diluent.

6. A composition suitable for controlling the growth of undesired vegetation which comprises an effective amount of the compound of claim 2 and at least one of the following: surfactant, solid or liquid diluent.

7. A composition suitable for controlling the growth of undesired vegetation which comprises an effective amount of the compound of claim 3 and at least one of the following: surfactant, solid or liquid diluent.

8. A composition suitable for controlling the growth of undesired vegetation which comprises an effective amount of the compound of claim 4 and at least one of the following: surfactant, solid or liquid diluent.

9. A method for controlling the growth of undesired vegetation which comprises applying to the locus to be protected an effective amount of a compound of claim 1.

10. A method for controlling the growth of undesired vegetation which comprises applying to the locus to be protected an effective amount of the compound of claim 2.

11. A method for controlling the growth of undesired vegetation which comprises applying to the locus to be protected an effective amount of the compound of claim 3.

12. A method for controlling the growth of undesired vegetation which comprises applying to the locus to be protected an effective amount of the compound of claim 4.

13. A method for controlling the growth of undesired vegetation in rape which comprises applying to the locus of the rape an effective amount of a compound of claim 1.

14. A method for controlling the growth of undesired vegetation in rape which comprises applying to the locus of the rape an effective amount of the compound of claim 2.

15. A method for controlling the growth of undesired vegetation in rape which comprises applying to the locus of the rape an effective amount of the compound of claim 3.

16. A method for controlling the growth of undesired vegetation in rape which comprises applying to the locus of the rape an effective amount of the compound of claim 4.

* * * * *